United States Patent

Hiejima

[11] Patent Number: 5,925,023
[45] Date of Patent: Jul. 20, 1999

[54] MULTI STAGE TYPE FLOW RATE SWITCHING DEVICE

[75] Inventor: Katsuhiro Hiejima, Osaka, Japan

[73] Assignee: Nissho Corporation, Osaka, Japan

[21] Appl. No.: 08/951,126

[22] Filed: Oct. 15, 1997

[30] Foreign Application Priority Data

Oct. 15, 1996 [JP] Japan ................................. 8-272702

[51] Int. Cl.$^6$ .................................................. A61M 5/00
[52] U.S. Cl. ................. 604/246; 604/250; 137/625.18; 251/7
[58] Field of Search ................. 604/27, 34, 49, 604/246, 250, 253, 30, 256; 251/4, 7; 137/595, 625.18

[56] References Cited

U.S. PATENT DOCUMENTS

| | | | |
|---|---|---|---|
| 4,688,753 | 8/1987 | Tseng et al. | 251/7 |
| 4,950,255 | 8/1990 | Brown et al. | 604/250 |
| 5,318,515 | 6/1994 | Wilk | 604/30 |

*Primary Examiner*—Wynn Wood Coggins
*Assistant Examiner*—LoAn H. Thanh
*Attorney, Agent, or Firm*—Kubovcik & Kubovcik

[57] ABSTRACT

A multi stage type flow rate switching device is provided which simplifies switching of flow paths and which rarely causes erroneous operation. The multi stage type flow rate switching device includes a liquid medicine flow inlet port 1 having branch paths 11, 12 and 13 on a downstream side, a liquid medicine flow outlet port 2 having branch paths 21, 22 and 23 on an upstream side and constant flow rate paths 31, 32 and 33 for connecting respective branch paths, and arranged in a housing 4 comprising a lid 41 and a housing main body 42. In the housing 4, there is provided clamping means 5 capable of selectively blocking the constant flow rate paths 31, 32 and 33.

1 Claim, 10 Drawing Sheets

Flow path 3
Flow path 2
Flow path 1
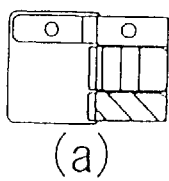 (a)  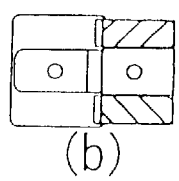 (b)  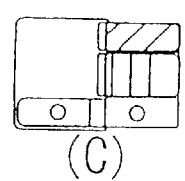 (C)  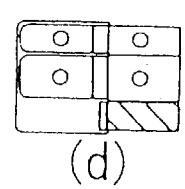 (d)
Flow path 3
Flow path 2
Flow path 1
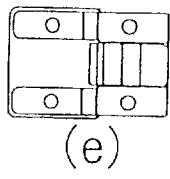 (e)  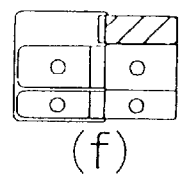 (f)  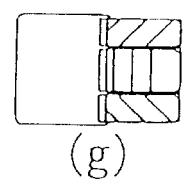 (g)  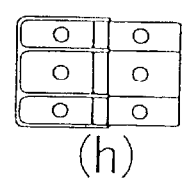 (h)
F I G. 5

MULTI STAGE TYPE FLOW RATE SWITCHING DEVICE

BACKGROUND OF THE INVENTION

1. Field of the Invention

The present invention relates to a multi stage type flow rate switching device. More particularly, the present invention relates to a multi stage type flow rate switching device suitable for controlling variably a small flow rate by being connected to a ballooned liquid medicine continuous injector (an injector where liquid medicine is filled in a balloon made of an elastic rubber material and liquid medicine is continuously injected over a period of many hours into a human body by utilizing the force produced by contraction of the balloon) that is used as a means for continuously administering a liquid analgetic, anesthetic, antibiotic, or carcinostatic agent into blood vessels, hypodermic portions, epidural portions or the like in a small amount.

2. Description of Related Art

With respect to a variable small flow rate control device used in a ballooned liquid medicine continuous injector, a device comprising flow rate control tubes connected to a multi-way stopcock has already been proposed (Japanese Unexamined Patent Publication No. JP-A-5-84310). The device is constituted by a main body having a cylindrical valve chamber where one flow inlet port and at least three flow outlet ports are formed. A plug having a cylindrical valve portion is rotatably inserted into the valve chamber of the main body. A slit opened in a fan-like shape and slender holes in a straight tube shape extending opposedly in a radial direction from the base of the slit are formed at the valve portion and, even if the slender holes of the valve portion are connected to any of the flow outlet ports, the slit is connected to the flow inlet port.

However, according to the above-described flow rate control device, one flow rate control tube is necessary for each flow outlet port and various sizes of the flow rate control tubes are necessary. It is troublesome in view of production control and assembly operation to fabricate various sizes of flow rate control tubes and integrate them simultaneously. Also, the use thereof involves a drawback where the switch angle of the lever is decreased for a large number of switchings and the display is complicated whereby erroneous operation is liable to occur.

The present invention has been achieved as a result of an intensive study in view of the above-described situation and it is an object of the present invention to provide a multi stage type flow rate switching device which simplifies production steps, which can be fabricated at a low cost and which simplifies switching of flow paths and rarely causes erroneous operation.

SUMMARY OF THE INVENTION

According to the present invention, there is provided a multi stage type flow rate switching device including a liquid medicine flow inlet port having plural branch paths on a downstream side, a liquid medicine flow outlet port having plural branch paths on an upstream side, constant flow rate paths for connecting the plural branch paths of the liquid medicine flow inlet port and the plural branch paths of the liquid medicine flow outlet port, and a housing comprising a lid and a main body capable of accommodating and arranging the constant flow rate paths. In the housing, there is provided a clamping means which is capable of selectively blocking the constant flow rate paths.

It is preferable that the clamping means of the present invention comprises flow path pressing means whose number is equal to the number of the constant flow rate paths and the flow path pressing means are provided opposite the constant flow rate paths. It is particularly preferable that the flow path pressing means are constituted by plural plate members provided foldably by hinges at the inside of the lid of the housing, and each of the plate members is provided with a pressing portion on one side thereof for blocking each of the constant flow rate paths. When a plate member is folded, the pressing portion is brought into a state of blocking a constant flow rate path and when the plate member is unfolded, the pressing portion is brought into a state of not blocking the constant flow rate path.

It is also preferable that the clamping means of the present invention is constituted by plural plate-like members having engaging means for engaging with the housing and insertable from a slit provided in the lid of the housing. The plate-like members are stepwisely provided with constant flow rate path blocking portions each having a relatively thick (or wide) wall and constant flow rate path nonblocking portions each having a relatively thin (or narrow) wall. Different desired flow rates can be selected by utilizing different kinds of the plate-like members each having a different stepped shape.

BRIEF DESCRIPTION OF THE DRAWINGS

FIGS. 5(a), 5(b), 5(c), 5(d), 5(e), 5(f), 5(g) and 5(h) are plane views showing combinations of the clamping means according to the present invention;

DETAILED DESCRIPTION OF THE PREFERRED EMBODIMENTS

Embodiments of the present invention are explained below with reference to the drawings.

Figure 1:
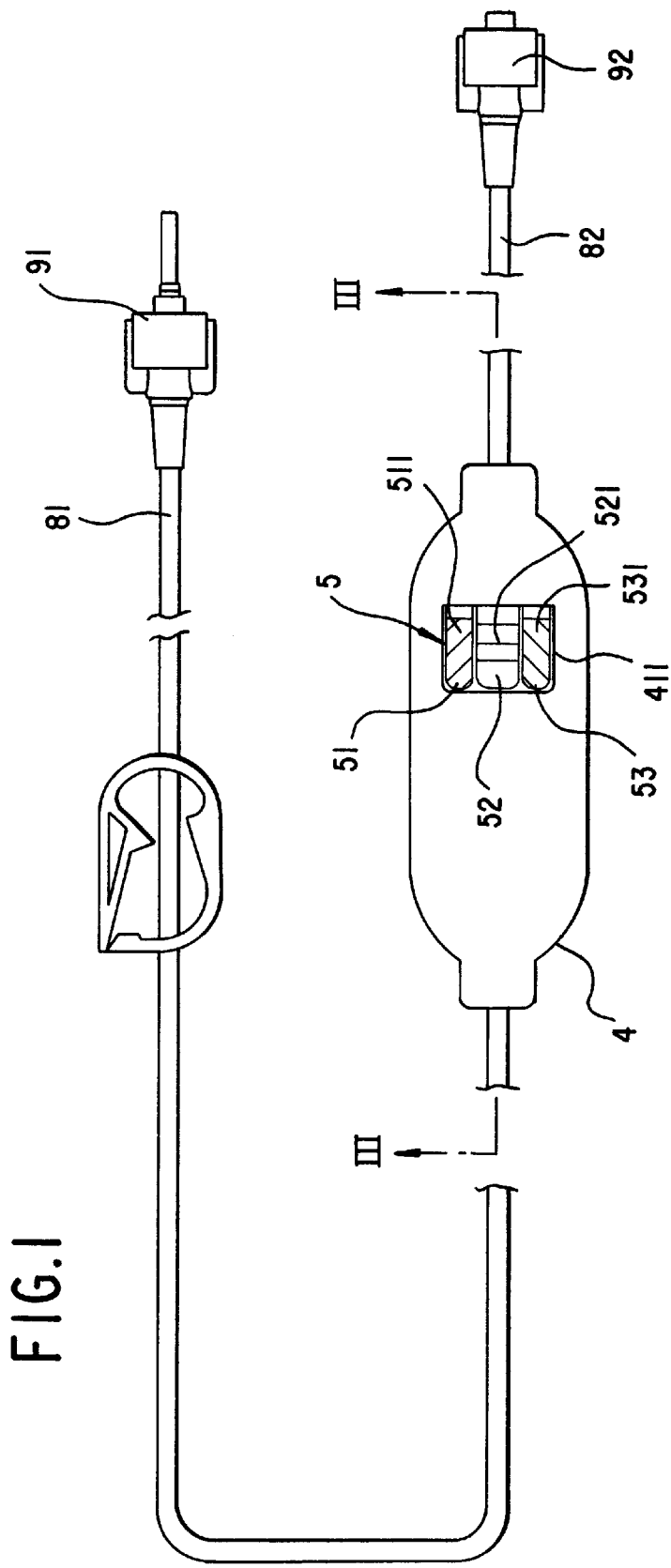
FIG. 1 is an explanatory view showing an embodiment of the multi stage type flow rate switching device according to the present invention (showing a state where a lid of a housing is closed)
Figure 2:
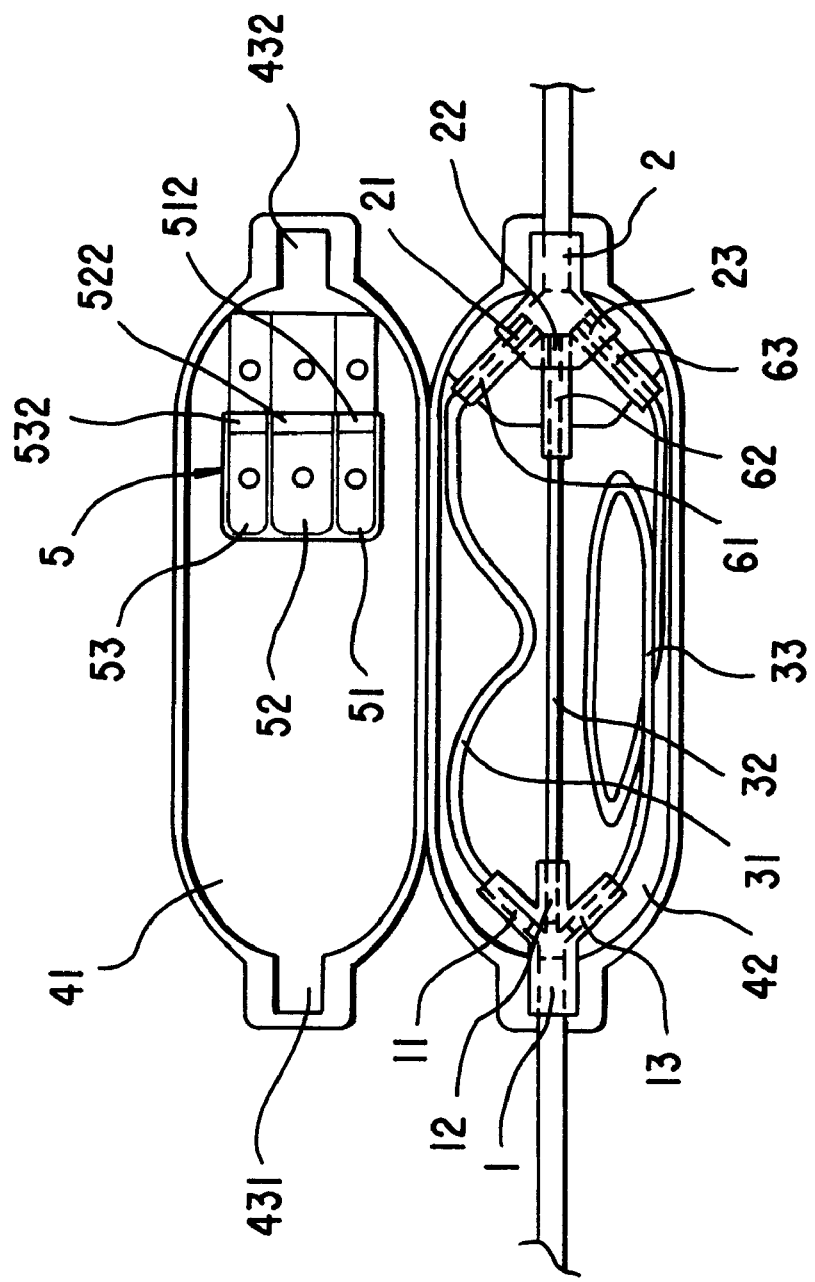
FIG. 2 is a plane view of essential portions of the multi stage type flow rate switching device shown in FIG. 1 (showing a state where the lid of the housing is opened)

As shown in FIG. 2, a multi stage type flow rate switching device of the present invention includes a liquid medicine flow inlet port 1 having three branch paths 11, 12 and 13 on a downstream side, a liquid medicine flow outlet port 2 having three branch paths 21, 22 and 23 on an upstream side, and a flow rate control unit where constant flow rate paths 31, 32 and 33 for connecting respectively the branch paths 11, 12 and 13 and the branch paths 21, 22 and 23, and which are accommodated and arranged in a housing 4 having an openable and closable lid 41. As shown in FIG. 1, tubes 81 and 82 are respectively attached to the liquid medicine flow inlet port 1 and the liquid medicine flow outlet port 2, and connectors 91 and 92 are respectively provided at other ends of the tubes 81 and 82. Here, the constant flow rate paths 31, 32 and 33 may be connected to the branch paths 11, 12 and 13 or the branch paths 21, 22 and 23 respectively through connection tubes 61, 62 and 63 which can be pressed and blocked by a clamping means 5. Although, according to the embodiment shown in FIG. 2, the constant flow rate paths 31, 32 and 33 are connected to the branch paths 21, 22 and 23 of the liquid medicine flow outlet port 2 through the connection tubes 61, 62 and 63, the connection tubes 61, 62 and 63 may be integrally formed with the branch paths 11, 12 and 13 of the liquid medicine flow inlet port 1 or the branch paths 21, 22 and 23 of the liquid medicine flow outlet port 2. Although the constant flow rate paths 31, 32 and 33 may be set at the same flow rate, it is preferable to set them at different flow rates if combinations of switching of flow rates are intended to increase in number. According to the embodiment shown in FIG. 2, the flow rates are made to differ from each other by changing lengths of the constant flow rate paths 31, 32 and 33. The number of the constant flow rate paths in the present invention is not limited to three and the number may be increased or decreased as necessary.

The housing 4 comprises the lid 41 and a housing main body 42. The lid 41 and the housing main body 42 are openable and closable by mutual engaging means. Incidentally, a locking means may be provided on the housing 4 so that a patient cannot open or close it easily. It is preferable that grooves 431 and 432 or the like are provided on the housing 4 so that the liquid medicine flow inlet port 1, the liquid medicine flow outlet port 2 and the constant flow rate paths 31, 32 and 33 are fixed in the housing 4.

Figure 3:
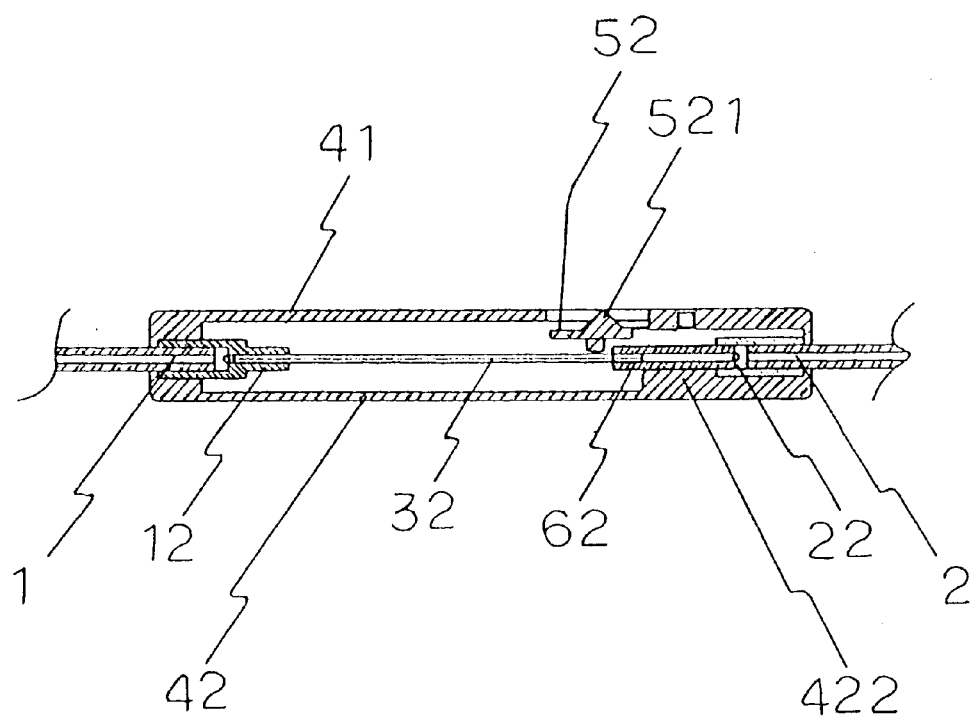
FIG. 3 is a sectional view taken along line III—III of the multi stage type flow rate switching device shown in FIG. 1.
Figure 4:
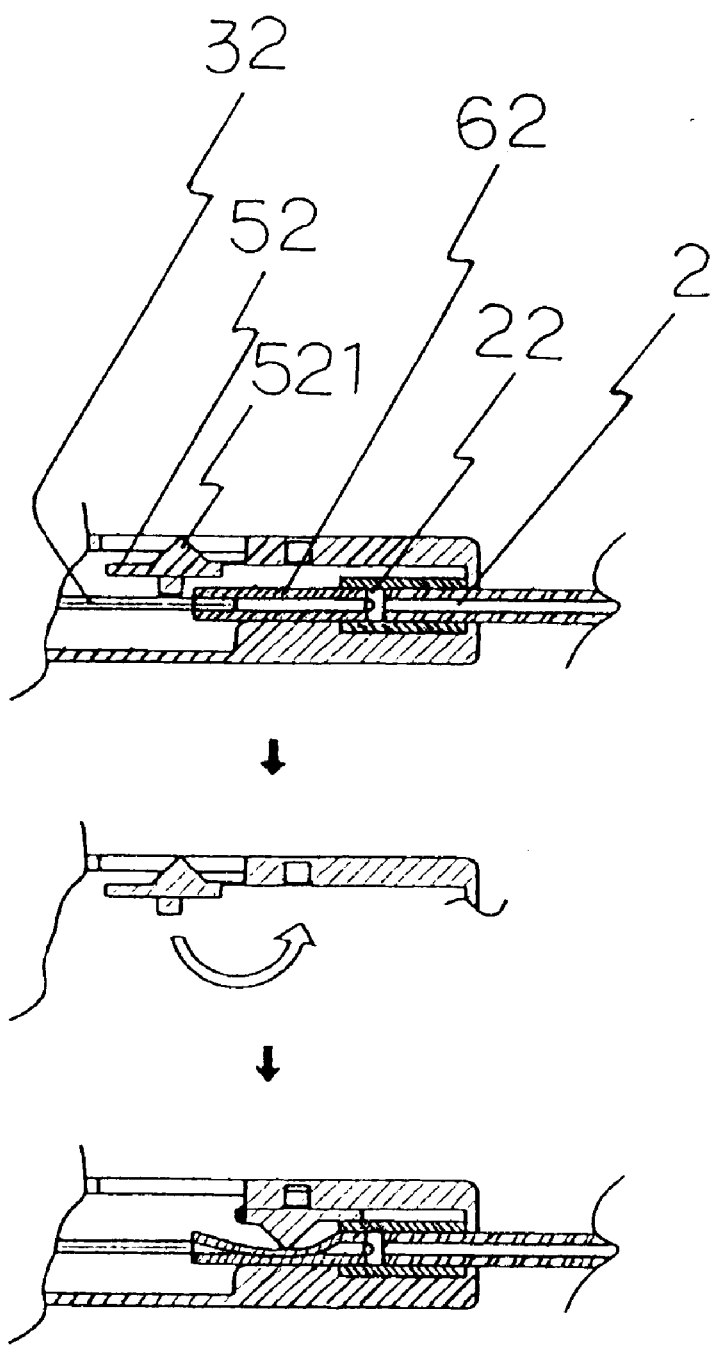
FIG. 4 is an explanatory view illustrating a flow rate switching operation of the multi stage type flow rate switching device shown in FIG. 1.

Further, as shown in FIGS. 1, 3 and 4, the clamping means 5 comprising plate members 51, 52 and 53 foldable by hinges 512, 522 and 532 are provided inside of the lid 41. The projections 511, 521 and 531 are respectively provided at one-side of faces of the plate members 51, 52 and 53 as pressing portions capable of blocking the constant flow rate paths 31, 32 and 33. The plate members 51, 52 and 53 are foldable when the housing 4 is opened. The plate members 51, 52 and 53 are arranged such that when they are folded, the projections 511, 521 and 531 block the constant flow rate paths 31, 32 and 33. Here, the back side of the projections 511, 521 and 531 of the plate member 51, 52 and 53 may be engaged with the inside of the lid 41, when the plate members 51, 52 and 53 are folded. For example, recesses (or projections) can be provided on the lid 41 and the plate members 51, 52 and 53 and these engage with each other.

Although the position of the clamping means 5 is not particularly limited as long as the constant flow rate paths 31, 32 and 33 (or connection tubes 61, 62 and 63) can be blocked at the position, in the case where the liquid medicine flow inlet port 1 and the liquid medicine flow outlet port 2 are fixed to the housing 4 as in the embodiment shown in FIG. 2, the clamping means 5 is preferably provided in the proximity of the liquid medicine flow inlet port 1 or the liquid medicine flow outlet port 2. In this case, the constant flow rate paths 31, 32 and 33 are preferably connected to the liquid medicine flow inlet port 1 or the liquid medicine flow outlet port 2 through the connection tubes 61, 62 and 63 where the clamping means 5 blocks the constant flow rate paths 31, 32 and 33 by pressing and blocking the connection tubes 61, 62 and 63.

The constant flow rate paths 31, 32 and 33 or the connection tubes 61, 62 and 63 which are pressed and blocked by the clamping means 5, are preferably formed by elastic tubes so that portions which have been blocked are restored to original shapes when the flow rate is switched. The connection tubes are preferably made of soft polyvinyl chloride, silicone rubber, thermoplastic elastomer or the like.

Further, although a window 411 is provided in the lid 41 according to the embodiment shown in FIGS. 1 and 2, the window is not particularly necessary as long as the constant flow rate paths 31, 32 and 33 are not likely to be pressed and blocked by the plate members 51, 52 and 53 when the constant flow rate paths 31, 32 and 33 are not in position to be pressed and blocked by the plate members 51, 52 and 53.

Further, the plate members 51, 52 and 53 of the embodiment shown in FIGS. 1–4 are integrally formed with the housing 4 and are foldable by forming hinges 512, 522 and 532 having a thin wall thickness. In this case, the material of which the housing 4 is formed is preferably made of a material capable of forming hinges 512, 522 and 532 such as polyethylene, polypropylene, polystyrene, hard polyvinyl chloride or the like. According to the present invention, the plate members 51, 52 and 53 may separately be formed and may be attached to the inside of the lid 41. Further, the clamping means 5 is not necessarily provided with the projections as long as the constant flow rate paths 31, 32 and 33 can be blocked. For example, the thicknesses of the plate members 51, 52 and 53 may be increased to a degree capable of blocking the constant flow rate paths 31, 32 and 33. Further, a rise portion 422 may be provided in the housing main body 42 to help block the constant flow rate paths 31, 32 and 33 by the projections 511, 521 and 531.

Explaining, in detail, the blocking mechanism of the present invention, as shown in FIG. 4, when the housing 4 is closed, the plate member 52 is brought into a state of not blocking the constant flow rate path 32. When the housing 4 is opened, the plate member 52 is brought into a state capable of being folded. When the plate member is folded by opening the housing 4 and then the housing 4 is closed, the constant flow rate path 32 is pressed and blocked. In order to set the flow rate of the flow rate switching device, there are eight possibilities as shown in FIGS. 5 (*a*), 5(*b*), 5(*c*), 5(*d*), 5(*e*), 5(*f*), 5(*g*) and 5(*h*). For example, in these drawings, FIG. 5(*a*) shows a state of the clamping means 5 blocking the constant flow rate paths 31 and 32. FIG. 5(*b*) shows a state of the clamping means 5 blocking the constant flow rate paths 31 and 33. FIG. 5(*c*) shows a state of the clamping means 5 blocking the constant flow rate paths 32 and 33. FIG. 5(*d*) shows the state of the clamping means 5 blocking the constant flow path 31. FIG. 5(*e*) shows a state of the clamping means 5 blocking the constant flow rate path 32. FIG. 5(*f*) shows the state of the clamping means 5 blocking the constant flow rate path 33. FIG. 5(*g*) shows a state of the clamping means 5 blocking all of the constant flow rate paths 31, 32 and 33. Further, FIG. 5(*h*) shows a state of the clamping means 5 where none of the constant flow rate paths 31, 32 and 33 are blocked.

Incidentally, the housing 4 according to the present invention can be used any number of times as long as the constant flow rate path blocking mechanism operates normally (as long as the hinges are not weakened to break).

Next, an explanation will be given of a second embodiment of a multi stage type flow rate switching device according to the present invention with reference to FIGS. 6–9.

Figure 6:
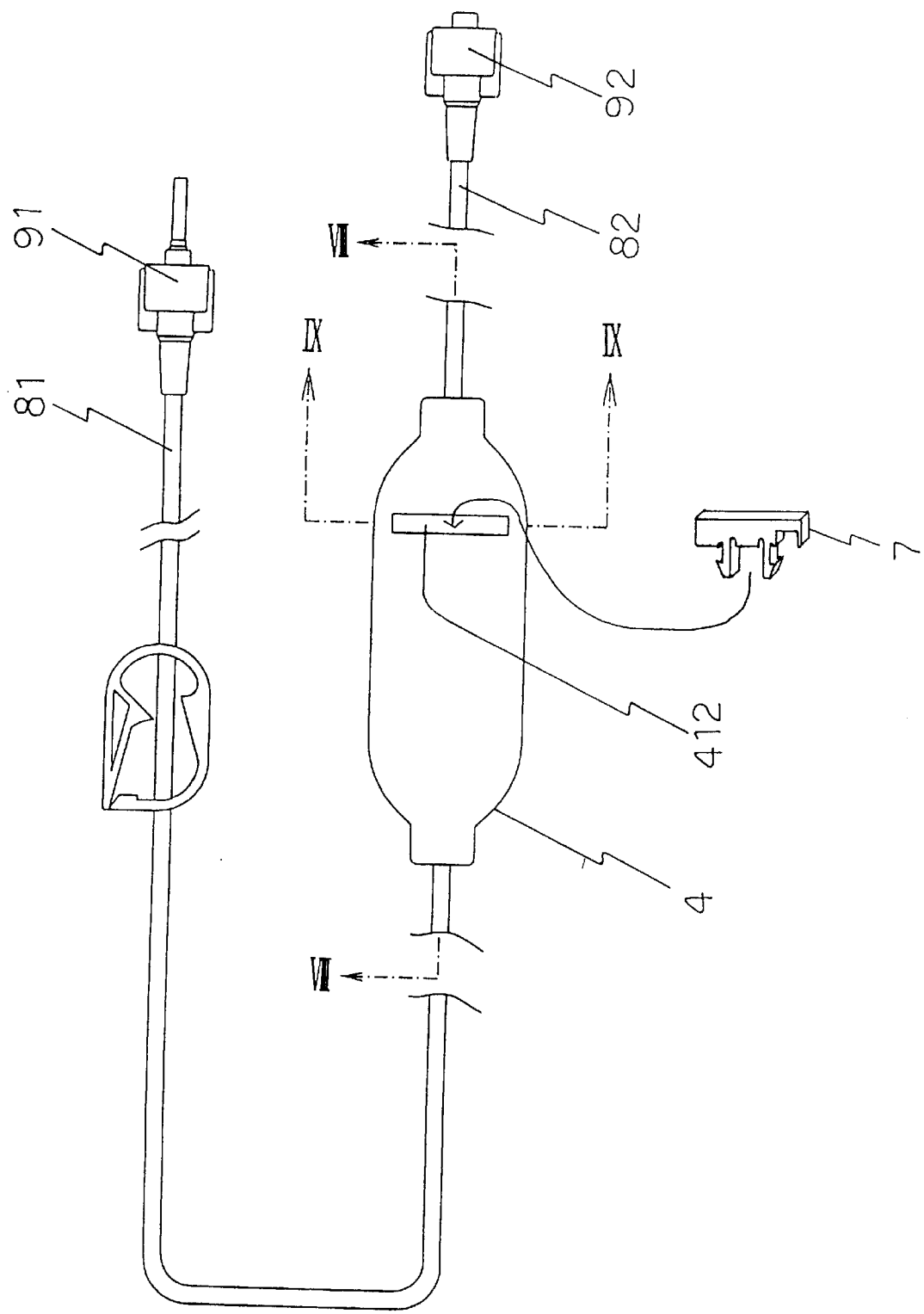
FIG. 6 is an explanatory view showing another embodiment of the multi stage type flow rate switching device according to the present invention (showing a state where a lid of a housing is closed)
Figure 7:
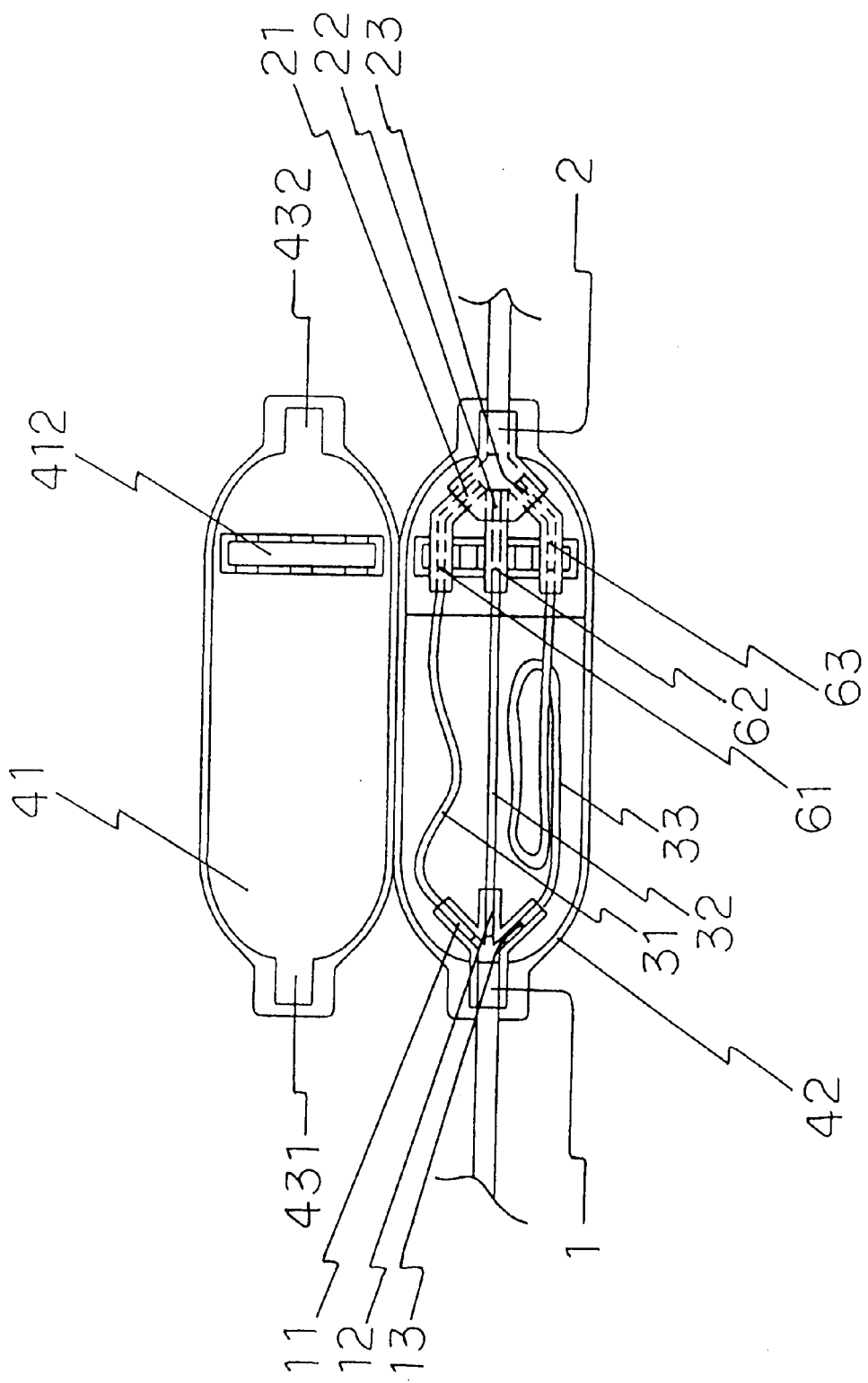
FIG. 7 is a plane view showing essential portions of the multi stage type f low rate switching device shown in FIG. 6 (showing a state where the lid of the housing is opened)
Figure 8:
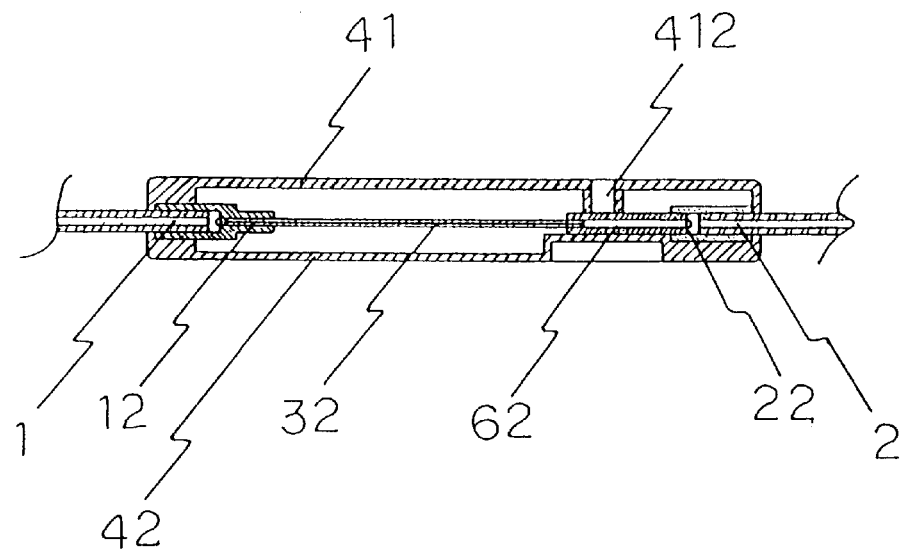
FIG. 8 is a sectional view taken along line VIII—VIII of the multi stage type f low rate switching device shown in FIG. 6.
Figure 9:
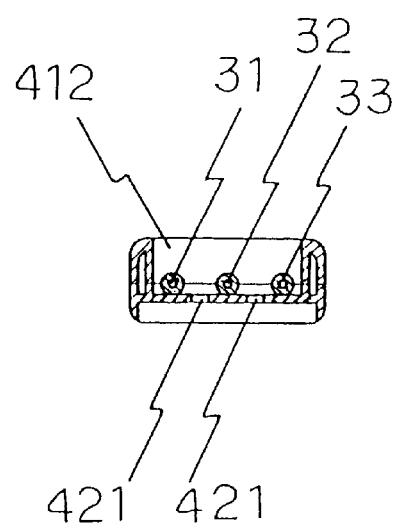
FIG. 9 is a sectional view taken along line IX—IX of the multi stage type flow rate switching device shown in FIG. 6.

FIG. 6 is an explanatory view showing other embodiment of a multi stage type flow rate switching device of the present invention (showing a state where a lid of a housing is closed), FIG. 7 is a plane view showing essential portions of the multi stage type flow rate switching device shown in FIG. 6 (showing a state where the lid of the housing is opened), FIG. 8 is a sectional view taken along a line VIII—VIII of the multi stage type f low rate switching device shown in FIG. 6 and FIG. 9 is a sectional view taken along a line IX—IX of the multi stage type flow rate switching device shown in FIG. 6.

According to the multi stage type flow rate switching device shown in FIG. 6, plate-like members 7 shown in FIGS. 10(a), 10(b), 10(c), 10(d), 10(e), 10(f) are adopted in place of the plate members 51, 52 and 53 constituting the clamping means 5 in FIG. 1. As shown in FIG. 6, a plate-like member inserting portion 412 capable of having the plate-like members 7 inserted therein is provided in the lid 41 of the housing 4. Although the position of the plate-like member inserting portion 412 is not particularly limited as long as it is a position where the plate-like members 7 can block the constant flow rate paths 31, 32 and 33 (or the connection tubes 61, 62 and 63), when the liquid medicine flow inlet port 1 and the liquid medicine flow outlet port 2 are fixed to the housing 4 as in this embodiment, the plate-like member inserting portion 412 is preferably provided in the proximity of the liquid medicine flow inlet port 1 or the liquid medicine flow outlet port 2. In this case, it is preferable that the constant flow rate paths 31, 32 and 33 are connected to the liquid medicine flow inlet port 1 or the liquid medicine flow outlet port 2 through the connection tubes 61, 62 and 63, where the plate-like members 7 block the connection tubes 61, 62 and 63.

Figure 10:
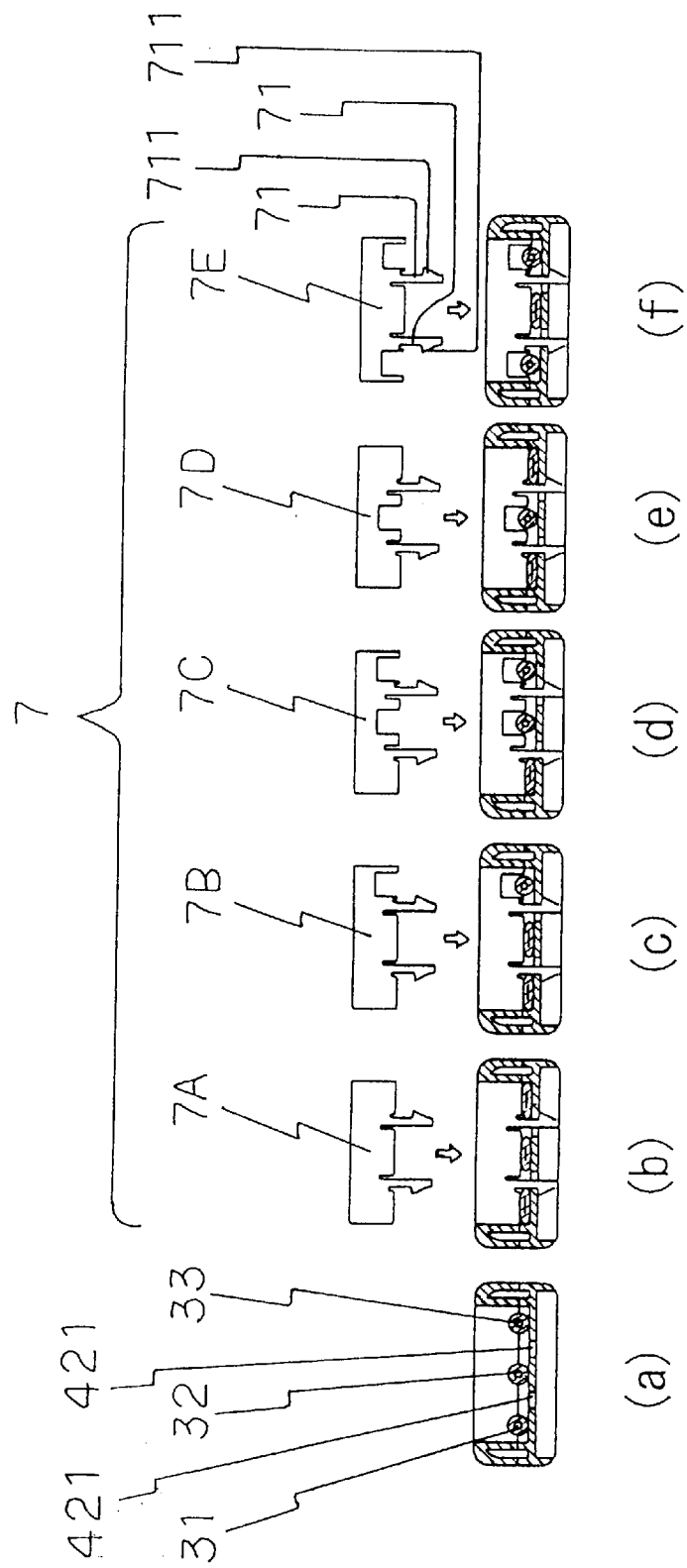
FIGS. 10(a), 10(b), 10(c), 10(d), 10(e) and 10(f) are explanatory views showing the insertion operation of the plate-like members used in the multi stage type flow rate switching device shown in FIG. 6.
Figure 11:
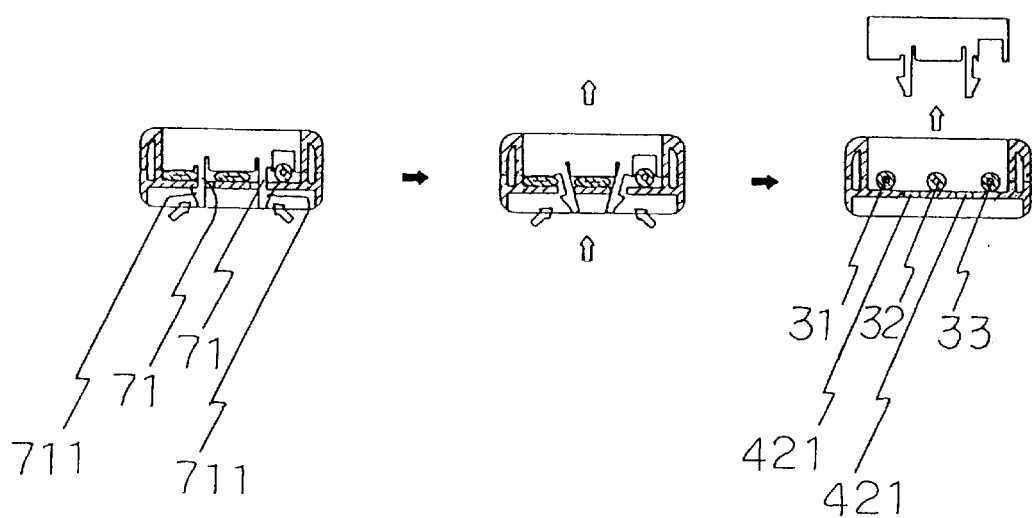
FIG. 11 is an explanatory view showing the operation of detaching a plate-like member that is inserted in FIGS. 10(a), 10(b), 10(c), 10(d), 10(e) and 10(f).

One or more constant flow rate path blocking portions each having a relatively thick (or wide) wall and one or more constant flow rate path nonblocking portions each having a relatively thin (or narrow) wall are stepwisely formed on each of the plate-like members 7. The flow rate is determined by selecting one of the plate-like members 7 according to a desired flow rate from several kinds of the plate-like members 7 each having a different stepped shape. Further, the plate-like member 7 is provided with a pair of engaging arms 71 and hooks 711 respectively formed at external sides of the side walls at front end portions of engaging arms 71. Engaging holes 421 for engaging with the engaging arms 71 of a plate-like member 7 are formed in the housing main body 42 whereby the engaging holes 421 are engaged with the hooks 711 of the engaging arms 71 when the plate-like member 7 is inserted. The engaging arms 71 can easily be bent toward the inner side because of the flexibility of the material forming the engaging arms 71. The engaging state can be released by bending the engaging arms 71 toward the inner side. Here, it is preferable that the vicinity of the engaging holes 421 of the housing main body 42 is formed in a shape recessed inwardly toward the housing 4 where fingers may be put therein. Thereby, the engagement of the engaging arms 71 and the engaging holes 421 is not released erroneously when the plate-like member 7 is inserted into the engaging holes 421 as shown in FIG. 10 and FIG. 11. Further, the plate-like member 7 is preferably provided with a length whereby the plate-like member 7 is inserted into the plate-like member inserting portion 412 to a position where the plate-like member 7 does not project from the plate-like member inserting portion 412. Incidentally, the engaging means is not limited to the shapes of the engaging arm 71 and the engaging hole 421 as described in this embodiment.

The multi stage type flow rate switching device of the second embodiment can switch the flow rate among eight different flow rates since the device has the three constant flow rate paths 31, 32 and 33. In this case, the plate-like member 7 can be used by reversing the left and right direction. Accordingly, five kinds of plate-like members 7A, 7B, 7C, 7D and 7E may be prepared as shown in FIGS. 10(a), 10(b), 10(c), 10(d) and 10(e).

Explaining, in detail, the blocking mechanism of the second embodiment, in order to set the flow rate of the flow rate switching device, a person selects one of the five kinds of plate-like members 7A, 7B, 7C, 7D and 7E shown in FIGS. 10(a), 10(b), 10(c), 10(d), 10(e) and 10(f) according to a desired flow rate, and inserts the selected plate-like member into the engaging holes 421. For example, in these drawings, FIG. 10(a) shows a state of the constant flow rate paths 31, 32 and 33 before blocking the flow paths. FIG. 10(b) shows a state where all of the constant flow rate paths 31, 32 and 33 are blocked. FIG. 10(c) shows the state where the constant flow rate paths 31 and 32 are blocked. FIG. 10(d) shows the state where the constant flow rate path 31 is blocked. FIG. 10(e) shows a state where the constant flow rate paths 31 and 33 are blocked. FIG. 10(f) shows a state where the constant flow rate path 32 is blocked. Further, in order to block the constant flow rate paths 32 and 33, the plate-like member 7B is reversed and inserted in FIG. 10(c). In order to block the constant flow rate path 33, the plate-like member 7C is reversed and inserted in FIG. 10(d). In detaching the plate-like member (for example 7B), as shown in FIG. 11, the pair of engaging arms 71 are bent inwardly, whereby the engagement is released.

Incidentally, the housing 4 according to the second embodiment can be used any number of times as long as the constant flow rate path blocking mechanism operates normally, that is, the engagement state of the engaging arms and the engaging holes is normal.

According to the multi stage type flow rate switching device of the present invention, the relationship between combinations of flow paths and the flow rate is as illustrated in Table 1 when the flow rates of the constant flow rate paths are set as follows.

TABLE 1

| Flow rate of each flow path | | Combinations of flow paths | | | | | | |
|---|---|---|---|---|---|---|---|---|
| | | 1 | 2 | 3 | 1 + 2 | 1 + 3 | 2 + 3 | 1 + 2 + 3 |
| Flow path 1 | 1 ml/hr | 1 | 2 | 4 | 3 | 5 | 6 | 7 |
| Flow path 2 | 2 ml/hr | | | | | | | |
| Flow path 3 | 4 ml/hr | | | | | | | |
| Flow path 1 | 2 ml/hr | 2 | 3 | 4 | 5 | 6 | 7 | 9 |
| Flow path 2 | 3 ml/hr | | | | | | | |
| Flow path 3 | 4 ml/hr | | | | | | | |
| Flow path 1 | 0.5 ml/hr | 0.5 | 1 | 2 | 1.5 | 2.5 | 3 | 3.5 |
| Flow path 2 | 1 ml/hr | | | | | | | |
| Flow path 3 | 2 ml/hr | | | | | | | |
| | | | | | | | | (ml/hr) |

As is apparent from the above-described explanation, the multi stage type flow rate switching device of the present invention is provided with a simple structure where the constant flow rate paths are pressed and blocked or closed by clamping means. Therefore, the present invention has advantages where the fabrication is facilitated and the device can be fabricated at a low cost. Further, flow path switching operation is simple and accordingly, erroneous operation is rarely caused.

What is claimed is:

1. A multi stage type flow rate switching device comprising:

a liquid medicine flow inlet port having plural branch paths on a downstream side;

a liquid medicine flow outlet port having plural branch paths on an upstream side;

constant flow rate paths for connecting the plural branch paths of the liquid medicine flow inlet port and the plural branch paths of the liquid medicine flow outlet port;

a housing comprising a lid and a main body, said housing being capable of accommodating and arranging the plurality of constant flow rate paths; and clamping means provided in the housing and being capable of selectively blocking one or more of the plural constant flow rate paths, said clamping means comprising plural plate members provided opposite the constant flow rate paths, wherein a number of said plural plate members is equal to a number of the plural constant flow rate paths, said plural plate members are foldably provided through hinges inside the lid of the housing, and each of the plate members is provided with a pressing portion for blocking each of the constant flow rate paths, wherein when a plate member is folded, said pressing portion is brought into a state of blocking a respective constant flow rate path, and when said plate member is unfolded, said pressing portion is brought into a state of not blocking said constant flow rate path.

* * * * *